US008800881B2

(12) United States Patent
Biset et al.

(10) Patent No.: US 8,800,881 B2
(45) Date of Patent: Aug. 12, 2014

(54) CASSETTE, WORKSTATION AND METHOD FOR MARKING CONTAINERS CONTAINING A LIQUID

(75) Inventors: Roland Biset, Leuven (BE); Francois Bidet, Bondues (FR)

(73) Assignee: Terumo BCT, Inc., Lakewood, CO (US)

( * ) Notice: Subject to any disclaimer, the term of this patent is extended or adjusted under 35 U.S.C. 154(b) by 0 days.

(21) Appl. No.: 13/806,300

(22) PCT Filed: Jun. 21, 2011

(86) PCT No.: PCT/EP2011/060309
§ 371 (c)(1),
(2), (4) Date: Dec. 21, 2012

(87) PCT Pub. No.: WO2011/161089
PCT Pub. Date: Dec. 29, 2011

(65) Prior Publication Data
US 2013/0105571 A1    May 2, 2013

(30) Foreign Application Priority Data

Jun. 22, 2010   (DE) .......................... 10 2010 030 370

(51) Int. Cl.
| G06K 19/06 | (2006.01) |
| G06F 17/00 | (2006.01) |
| A61M 1/36  | (2006.01) |
| A61M 1/02  | (2006.01) |

(52) U.S. Cl.
CPC ............ *G06F 17/00* (2013.01); *A61M 2205/12* (2013.01); *A61J 2205/60* (2013.01); *A61M 1/3696* (2013.01); *A61M 1/0209* (2013.01); *A61M 2205/6054* (2013.01); *A61M 2205/3393* (2013.01)
USPC ......................................... 235/492; 235/375

(58) Field of Classification Search
USPC ................................................ 235/492, 375
See application file for complete search history.

(56) References Cited

U.S. PATENT DOCUMENTS

| 5,653,887 A  | 8/1997 | Wahl et al. |
| 7,776,601 B2 | 8/2010 | De Gaulle et al. |

(Continued)

FOREIGN PATENT DOCUMENTS

| EP | 1627651 A2 | 2/2006 |
| ES | 2270543 T3 | 4/2007 |

(Continued)

OTHER PUBLICATIONS

International Search Report, PCT/EP2011/060309, Oct. 3, 2011.

(Continued)

*Primary Examiner* — Kristy A Haupt
(74) *Attorney, Agent, or Firm* — John R. Merkling (57) ABSTRACT

The invention pertains to a cassette (1) provided as a cover of an accommodation section of a container (3) which can be filled with a liquid separable into individual components by means of a centrifuge, having: a plurality of containers (3, 5, 7) where a central container (3) is fixedly arranged at the cassette (1) and said central container (3) is connected to at least one outer container (5, 7) through interruptible connection means (15, 17, 11), and a data storage device (19) arranged on the cassette (1) or on the central container (3). Furthermore, the invention pertains to a workstation for marking containers (5, 7) containing a liquid and a corresponding method.

10 Claims, 4 Drawing Sheets

(56) References Cited

U.S. PATENT DOCUMENTS

2003/0072676 A1* 4/2003 Fletcher-Haynes et al. .... 422/23
2010/0133203 A1* 6/2010 Walker et al. ............ 210/748.11

FOREIGN PATENT DOCUMENTS

FR 2796182 A1 1/2001
FR 2825637 A1 12/2002

OTHER PUBLICATIONS

Notification of Transmittal of the International Preliminary Report on Patentability, PCT/EP2011/060309, Dec. 12, 2012.

Written Opinion of the International Searching Authority, PCT/EP2011/060309, Dec. 12, 2012.

* cited by examiner

CASSETTE, WORKSTATION AND METHOD FOR MARKING CONTAINERS CONTAINING A LIQUID

The invention relates to a cassette provided as a cover of an accommodation section of a container which can be filled with a liquid separable into individual components by means of a centrifuge, a workstation for marking containers containing a liquid and a method for marking containers containing a liquid.

In transfusion medicine, since the beginning of the nineties, the so-called blood component therapy has been successful. This means that, instead of a whole unit of stored blood, a patient is only given the blood components he/she individually needs. This separate administration of the individual blood components makes it possible to optimally treat on average 1.8 patients with one single unit of stored blood.

The essential blood components comprise the red blood corpuscles in the so-called erythrocyte concentrate that are transfused after a severe loss of blood to maintain the oxygen supply, the blood platelets in the thrombocyte concentrate that are administered in the event of coagulopathy (hemophilia) and the blood plasma that is administered in the event of coagulopathy and volume deficit. Apart from this, blood plasma is an essential basis for the production of numerous medicines.

The separation of the individual blood components which is called cell harvesting is effected, as known, by treatment of the blood in a centrifuge. By centrifuging, the individual blood components are separated from each other and can, then, be separately filled into suitable containers and separately used.

In this connection, however, the assignment of the donor's data such as age, blood group, gender etc. to the end product represents an essential problem. By a repeated transmission of these data, there is a great risk of an erroneous transmission, which might cause a wrong marking of the end product. A checking of the correct data transmission is only possible at a high expenditure or even is not possible at all.

Therefore, there is a need to create devices and methods ensuring a reliable data transmission over a plurality of processing steps.

A cassette according to the invention provided as a cover of an accommodation section of a container which can be filled with a liquid separable into individual components additionally includes a plurality of containers. A central container thereof is arranged at the cassette. The central container is connected to at least one outer container through interruptible connection means. Besides, a data storage device is arranged at the cassette or at one of the containers.

As, in case the liquid concerned is blood, the central container serves for receiving the donated blood, while the other containers serve for, after a centrifugation, receiving the blood products such as the erythrocyte concentrate (red blood corpuscles) or the plasma the cassette according to the invention represents a closed system. As the said closed system also comprises the data storage device it is ensured that the respective containers containing the respective blood products, erythrocyte concentrate and plasma remain correctly assigned to the data about the donor. Therefore, it is absolutely impossible that, during further processing of the donated blood, an end product is erroneously assigned and incorrect data are indicated on one of the end products.

Advantageously, the at least one outer container can be connected to an additional end product container, and a filter can be provided between the outer container and the end product container. Therefore, if required, it is possible to filter a blood product such as the erythrocyte concentrate after the centrifugation is finished and to gather the filtered erythrocyte concentrate in a separate end product container.

Advantageously, the containers and the end product container can be provided in the form of bags or bottles. Besides, the connection means can be provided as tubes partially positioned in a product conveying path formed in the cassette.

Although the containers are preferably provided as bags, it is possible to provide in particular the outer containers also in the form of e.g. bottles, this making a later marking easier. The bottles can be made of a synthetic material or glass. Alternatively, also boxes made of coated paper or coated cardboard can be used as containers. However, the use of bags is advantageous because they are soft. Therefore, it is possible to provide such bags in a vacuous state and, then, to fill them with the liquid without a discharge of air in the bags causing a problem. Advantageously, however, at best, required solutions such as anticoagulants and/or preservation solutions can be provided in the bags.

Advantageously, the data storage device can be part of an RFID tag. This allows a contact-less data storage and/or data detection. Alternatively, the data storage device can also be provided in the form of a tag attached to the cassette or one of the containers and the data can be printed thereon. The data can also be printed in the form of a bar code.

Besides, the RFID tag can also be integrated into the cassette or into one of the containers and can have an at least once writable memory. Thus, the RFID tag is inseparably connected to the system, which likewise ensures a permanently correct assignment of the data.

Besides, the invention relates to a workstation for marking containers containing a liquid. Same has a connection surface for a cassette as described above. In addition, the connection surface has a data detection device for detecting the data of the data storage device which is provided at the cassette. Besides, it has at least two trays for depositing respectively one outer container containing a liquid. Besides, to each tray, a second data detection device is assigned in order to detect data of the respective outer container. A data processing device serves for processing the data detected by the data detection device and the respective second data detection devices. Besides, to each tray, a marking device is assigned to mark the respective outer container. The marking device is designed for marking a medium with data.

While in the whole application the term "connection surface" is used, it is noted that the connection surface according to the invention, apart from having a flat shape, can have any other suitable shape such as an accommodation section or a slot for inserting the cassette or it can have the negative shape of the cassette. Preferably, the connection surface may have the shape of an insert as disclosed by the applicant in document DE 10 2007 000 308 A1. The insert serves to accommodate the containers during a centrifugal process, while the cassette can have a function to replace the cover of the insert in the above-mentioned prior art document.

By means of such a workstation, advantageously it is possible to detect the data stored in the storage device of the cassette and to assign them to the outer containers containing a liquid. This is advantageously effected by a data processing device which combines data detected by the outer containers such as the weight of the container with the data of the data storage of the cassette and outputs them to a medium through the marking device.

Advantageously, the respective second data detection device can be designed as scales detecting a weight of the container deposited on the respective tray. In particular in the production of blood products, it is advantageous to exactly know the weight of the product. The weight of the individual containers can then be output to the medium together with the other data by means of the marking device.

Advantageously, in addition, to each tray, a separation device can be assigned for separating a connection means between the outer containers and a central container arranged at the cassette. The separating device can also be designed for sealing the interior of the container against the surrounding area in a fluid-tight manner during separation.

By means of the separation device, it is possible to separate the individual containers from the other containers and/or the cassette so that a separate further processing of the individual products is possible. By sealing the connection means which can be advantageously designed as tubes while the containers can be advantageously designed as bags or bottles, a leaking out of the content of the containers is advantageously prevented.

Advantageously, the data detection device can be designed as an RFID reading apparatus. Advantageously, the separation device can be designed as a hot-cutting and sealing device which is adapted to separate the tube by applying heat and to simultaneously seal it. Besides, advantageously, the marking device can be designed for attaching the medium provided with the data to the container. Such mediums can be for example paper tags onto which the data are printed by means of the marking device. The paper tags can then be automatically or manually attached to the containers. The mediums can also be for example further RFID tags in the memory of which the respective data are written and which are attached to the respective containers. But also the container itself can serve as a medium. In this case, the marking with data is effected directly by the marking device on the respective containers. For example, the outer containers can be provided with blank RFID tags from the beginning, into the memories of which the marking device can write the corresponding data. Alternatively or additionally, the marking can be effected by thermally active means such as laser beams or marking stamps which mark the material of the container by thermal modification.

In particular, the connection surface can have a guiding means which enables the cassette to be inserted in a distinct predetermined manner, thereby preventing that the cassette is inserted in a different manner. Since the cassette, due to the guiding means which is also provided on it, can be inserted into the workstation only in a unique manner, it is ensured that the same outer container is always deposited on the same side of the workstation, and, thereby an accidental interchange of the outer containers is prevented. This can be especially important with blood products, if one of the containers contains plasma while the other container contains the erythrocyte.

For example, the guiding means can be formed as guiding recesses or grooves and guiding protrusions at the connection surface and at the cassette, respectively. Alternatively, the connection surface can be formed in a negative shape of the cassette, such that the cassette can be inserted into the connection surface merely by establishing a positive fit.

Preferably, however, a cassette according to the invention is used together with an insert as disclosed by the applicant in document DE 10 2007 000 308 A1. That is, instead of a cover disclosed in said document, the cassette according to the invention is used. In this preferred case, the connection surface has the negative shape of the insert.

Thus, the insert having the cassette attached to it and the respective containers housed in the corresponding chambers of the insert can serve as guiding means according to the invention. In this case, after removing the insert from the centrifuge, it can be inserted again into the connection surface in a unique manner.

Therefore, the outer containers are always arranged at the same locations in the insert, and removing them from the insert and depositing them on the assigned portions of the workstation can be performed in a facilitated manner. Thereby, the risk that the outer containers are interchanged and deposited in a false manner can be excluded.

In the event that tags are used also suitable reading devices such as bar code readers can be provided.

A method according to the invention for marking containers filled with a liquid comprises the following steps:

a) insertion of a cassette provided with a data storage device into a connection surface of a workstation;

b) detection of the data stored in the data storage device by means of a data detection device;

c) depositing at least one container connected, through a connection means, to a central container provided at the cassette and filled with a liquid on a respective tray;

d) detection of data of the container by means of a second data detection device which is assigned to the respective tray;

e) processing the data detected by the data detection device and the second data detection devices by means of a data processing device;

f) providing a medium with the processing data by means of a marking device assigned to the respective tray;

g) attaching the medium to a container deposited on the tray;

h) separation of the connection means and fluid-tight sealing of the respective container against the surrounding area by means of a separation device assigned to each tray.

By the method according to the invention, it is possible to mark all outer containers of a cassette according to the invention with the respective processing data without the risk of confusion or other errors. After the marking step and/or the attachment of the medium provided with markings, an immediate further processing of the containers is possible.

Advantageously, the data detection device can be provided as an RFID reading apparatus. The second data detection device can be advantageously provided as scales. The containers can be advantageously provided as bags and/or bottles while the connection means can be advantageously provided as tubes. The separation device can be advantageously provided as a hot-cutting and sealing device. The marking device can be advantageously provided as a printing and/or labeling device or as an RFID writing device.

Step g) can be advantageously effected by automatically or manually attaching tags on which the processing data are printed or RFID tags on which the processing data are written to the respective container. The processing data can include the data detected by the RFID reading apparatus and the weight detected by the pair of scales. Step g) can be alternatively effected by a direct effect in particular produced by heat e.g. by means of laser beams or marking stamps onto the material of the container.

Advantageously, a container filled with a liquid and an empty container connected to the latter can be deposited on a tray, and the scales can detect the total weight of the two containers.

Consequently, according to the invention, i.a. the weight of each outer container and/or of each outer container and an additional container connected therewith is detected. As the container weights are known an exact determination of the weights of the liquids in the respective containers is possible. If, before the method according to the invention is performed, the total weight of the cassette with all bags is established it is also possible to determine the weight of the liquid left in the central bag.

Although the invention is of special advantage for the preparation of blood products it has to be pointed out that the liquids in the central and in the outer containers do not necessarily have to be blood or blood products such as erythrocyte concentrate or plasma. According to the invention, it is possible, to process and then mark any liquid whose individual components can be separated by means of a centrifuge.

Embodiments of the invention preferred at present are described by referring to the figures attached hereto. The figures show.

Figure 1:
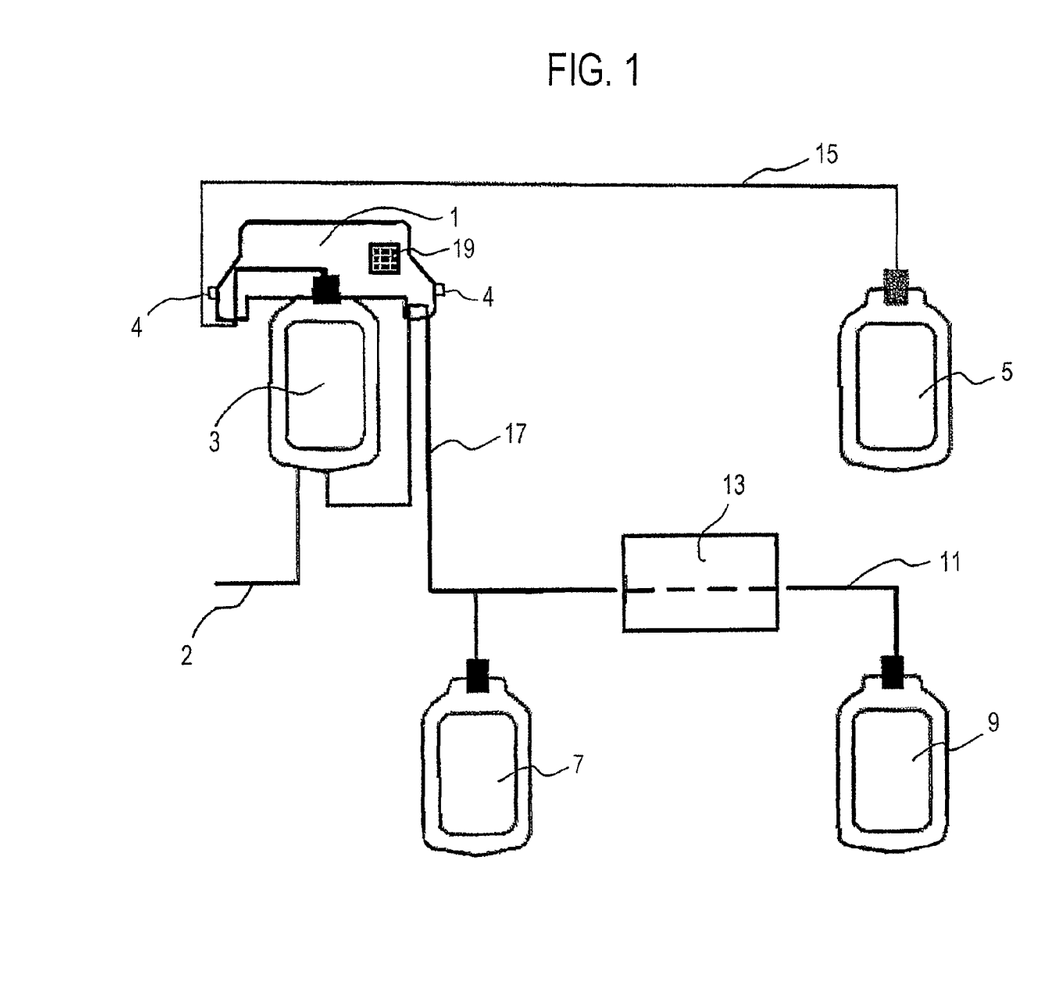
FIG. 1 a schematic view of a cassette according to the invention for the preparation of blood products.

FIG. 1 shows a cassette 1 according to an embodiment of the invention. At the cassette 1, there is a donation bag 3 serving as a central bag according to the invention. The donation bag 3 includes tubes 15, 17 serving as connection means to product bags 5 and 7 serving as outer bags. The donation bag 3 is fastened to the cassette 1 in a non-detachable manner. The tubes 15, 17 are partially positioned in product conveying paths provided in the cassette 1 and further extend to the product bags 5 and 7 which serve as outer bags according to the invention. A tube 2 serves for supplying blood into the donation bag 3 during a blood donation. Tube clamps not shown in FIG. 1 serve for cutting off the tubes 15 and 16. Besides, an RFID tag 19 is integrated into the cassette 1. Provided on two sides of the cassette 1, there are protrusions 4 serving as guiding means according to the invention, which can be brought into engagement with recesses 104 of a connection surface 103 being described later on the basis of FIG. 2. Therefore, the cassette 1 can be inserted into the connection surface 103 merely in a unique manner.

The cassette 1 according to the embodiment is especially provided for being used during a blood donation process and for serving as a cover of an accommodation section of a centrifuge accommodating the donation bag 3 in a centrifuging process for the production of blood products. During a blood donation process, the data of the donor and the donation are written into the memory of the RFID tag 19 within the framework of the donation process. In this case, the blood of the donor is supplied into the donation bag 3 through a needle and the tube 2. After completion of the donation, the tube 2 is clamped and/or separated from the donation bag 3 and, at the same time, sealed, which makes the handling easier and reduces the risk of injury caused by the needle. As, likewise, the tube clamps at the tubes 15 and 17 remain closed the donated blood remains in the donation bag 3 for further processing, i.e. the following centrifuging process.

After completion of the donation, the blood is separated into its individual components by means of a known centrifuging process. These are the red blood corpuscles in the erythrocyte concentrate, the blood plasma and the blood platelets in the thrombocyte concentrate (buffy-coat).

By applying pressure to the donation bag 3 during the centrifuging process and by opening the corresponding tube clamps, the plasma is fed through the tube 15 into the product bag 5 and, then, the erythrocyte concentrate is fed through tube 17 into the product bag 7. A known method for the preparation of in particular the plasma, which is applicable within the framework of this invention, is known from e.g. the German patent application laid open document DE 10 2007 000 309 A1. By closing the tube clamps, it is ensured that there is no reflux of the blood products from the products bags 5, 7. After the centrifuging process, the buffy-coat containing the platelets remains in the donation bag 3.

Through a further tube 11 and a filter 13, there is a connection from the product bag 7 to a second product bag 9. The tube 11 can be, likewise, cut off by a tube clamp or other means, which ensures that the erythrocyte concentrate remains in the product bag 7 during the centrifuging process.

After completion of the centrifuging process and removal of the cassette with the bags 3, 5 and 7 from the centrifuge, it is possible, at any time, to subject the erythrocyte concentrate in the product bag 7 to a filtration through the filter 13, and to supply the filtered erythrocyte concentrate to the second product bag 9.

Figure 2:
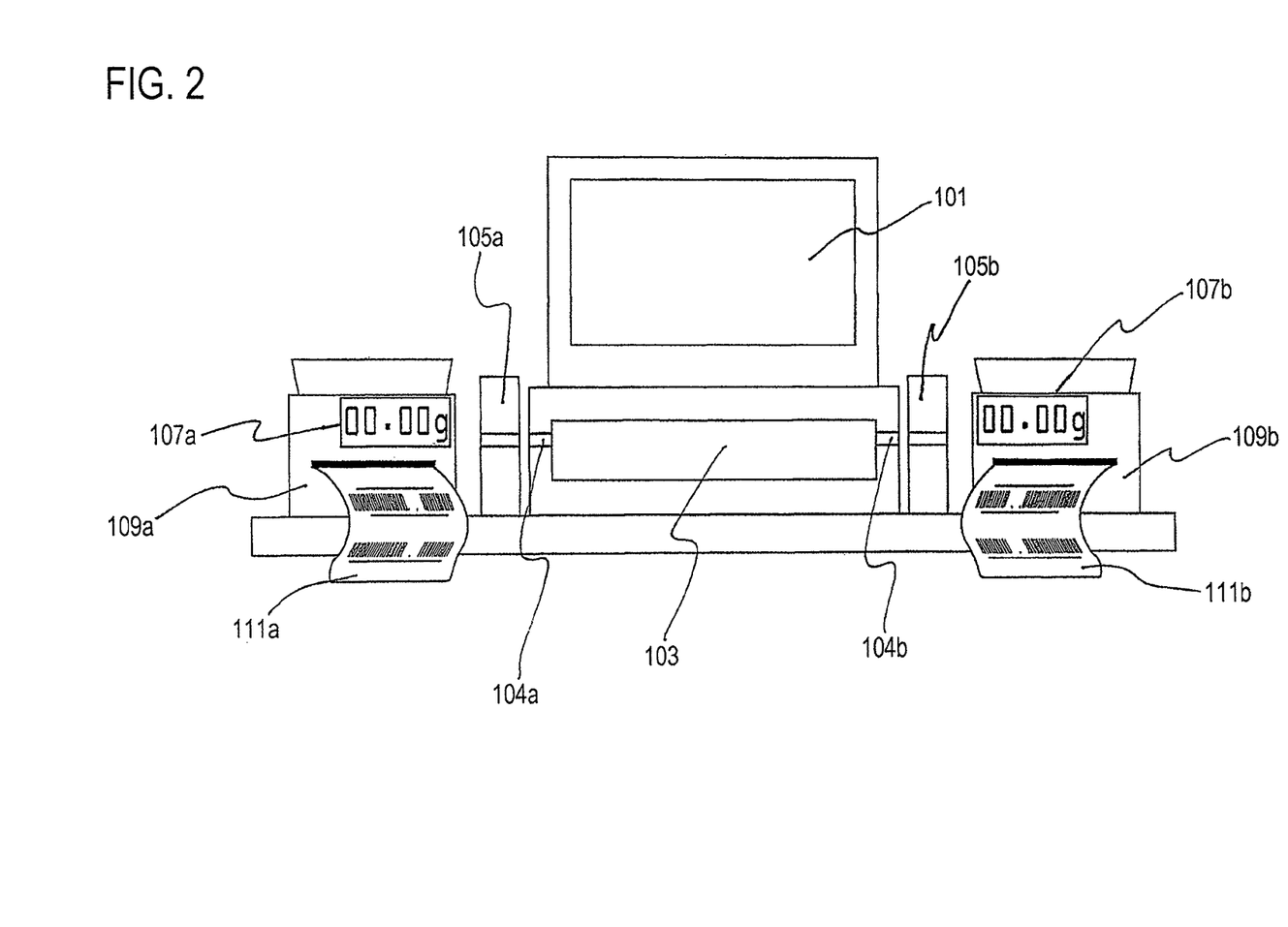
FIG. 2 a schematic view of a workstation according to the invention.

FIG. 2 shows a workstation according to the invention which serves for marking the blood products prepared according to the description above.

The workstation has an accommodation section 103 for the cassette 1 which serves as connection surface according to the invention. Recesses 104 form guiding means according to the invention and serve to receive the protrusions 4 of the cassette 1. Due to the positions of the recesses 104 at the accommodation section 103 and of the protrusions 4 on the cassette 1, the cassette 1 can be inserted into the accommodation section 103 merely in a unique manner.

A display 101 e.g. in the form of a screen which can also be provided as a so-called touch screen serves for displaying different method steps to a user. In the accommodation section 103, an RFID reading device is arranged as a data detection device according to the invention, which is provided to read-in the data from the RFID tag of the cassette 1. At the side of the accommodation section 103, there are separating and sealing devices 105a, 105b having an accommodation section for tubes 15 and/or 17. Following the separating and sealing sections, scales 107a and/or 107b are arranged, which serve as trays and as second data detection devices according to the invention. Within the area of the scales 107a and/or 107b, besides, tag printers 109a and/or 109b are arranged, which are provided to print data on tags 111a and/or 111b.

In the following, a presently preferred method for marking product bags according to the invention is described.

A user inserts a cassette 1 into the accommodation section 103 of the workstation, which serves as a connection surface according to the invention. After insertion of the cassette, the data stored in the memory of the RFID tag are read into the workstation by a control device. In the next step, the user puts the product bag 5 containing the plasma onto the pair of scales 107a and positions the tube 15 in the separating and sealing device 105a. Then, the user puts the product bag 7 containing the erythrocyte concentrate on the pair of scales 107b together with the tube 19, the filter 13 and the second product bag 9 and positions the tube 17 in a corresponding recess of the separating and sealing device 105b. If necessary, in addition, an additive solution for the preservation of the red blood corpuscles can be provided at the product bag 7 or 9 containing the erythrocyte concentrate. In the next step, the user starts an automatic separating and weighing operation by pressing a key on the workstation.

By the guiding means 4, 104 according to the invention it is ensured that the product bag 5 containing the plasma is deposited on scales 107a and that the product bag 7 containing the erythrocyte concentrate is deposited on scales 107b. Thus, depositing the product bags 5, 7 on a wrong side of the workstation, is excluded.

By means of the scales 107a and 107b, the weights of the product bag 5 with the plasma and/or of the product bag 7 with the erythrocyte concentrate including the tube 19, filter 13 and second product bag 9 are determined. The control device detects the two weights and outputs the donor data read by the RFID tag 19 together with the weight of the product bag 5 to the labeling device 109a which prints the data on a tag 111a and outputs the tag. The donor data including the weight of the product bag 7 of the tube 19, of the filter 13 and of the second product bag 9 are output to the labeling device 109b, by which the data are printed on a tag 111b. The user, then, after a check of the data which might be necessary, sticks the tags 111a and/or 111b on the product bag 5 and/or the product bag 7 or the second product bag 9. The tubes 15 and 17 are detached and sealed by the separating and sealing sections 105a and 105b.

After that, the product bags and the cassette including the donation bag in which the buffy coat is arranged are removed from the workstation and supplied to a further processing.

According to a further embodiment not shown in the figures, the data are not printed on tags 111a and 111b but written into a memory of RFID tags which are, then, attached to the product bag 5 containing the plasma and to the second product bag 9. After a filtering process where the erythrocyte concentrate in the product bag 7 was fed, through the tube 19 and the filter 13, into the second product bag 9, the latter is again weighed and the weight value in the memory of the RFID tag is overwritten.

A cassette and workstation according to the invention as well as the method according to the invention ensure that the correct donor data including the weight data of the products are unquestionably assigned to the respective product bags, and that errors in assigning the data are excluded. Therefore, the risk of incorrectly labeled product bags can be excluded.

Figure 3:
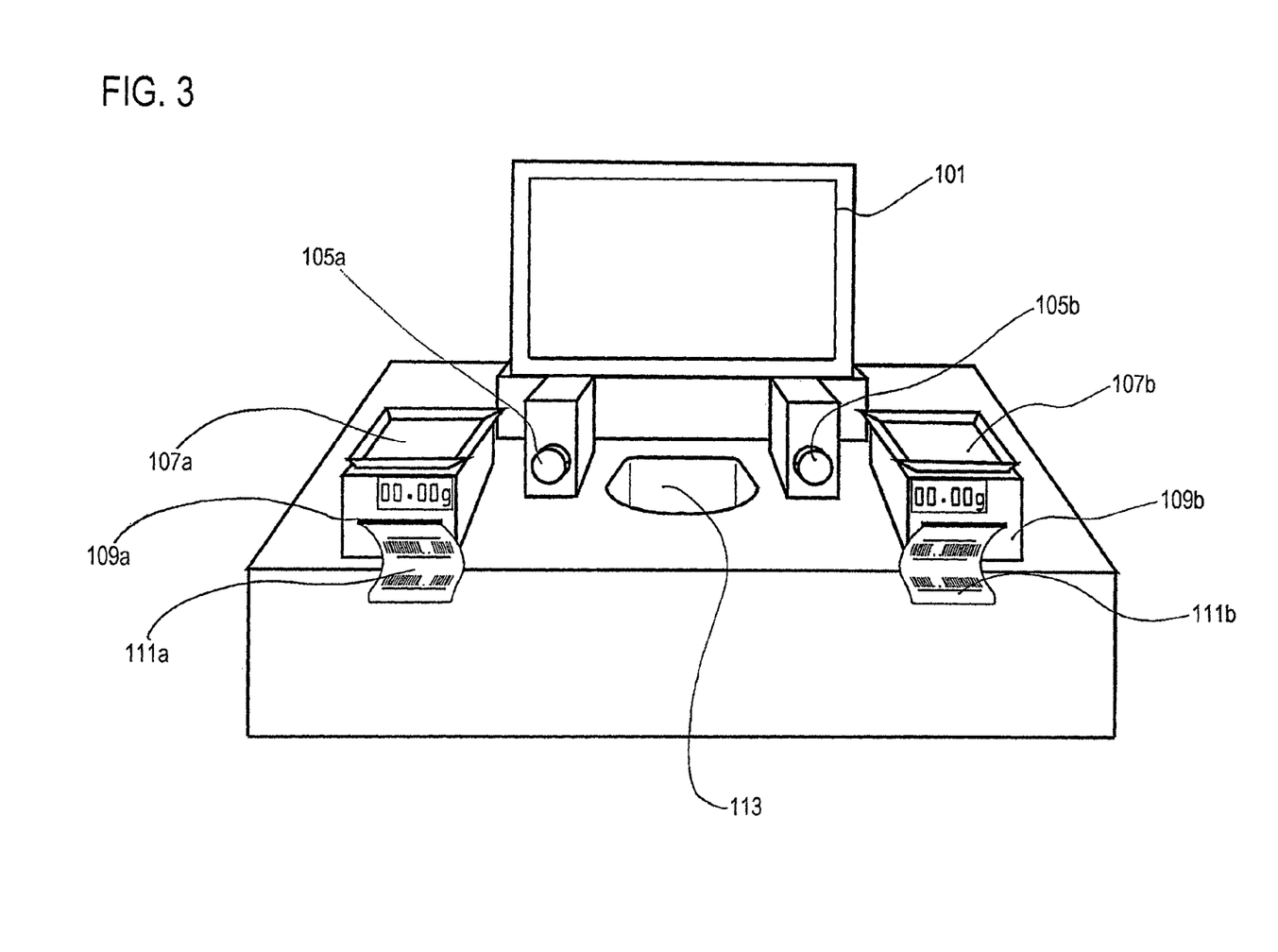
FIG. 3 shows a schematic perspective view of a presently preferred embodiment of a workstation according to the invention.

FIG. 3 shows a schematic perspective view of a presently preferred embodiment of a workstation according to the invention. Instead of the accommodation section 103 in FIG. 2, in this embodiment a slot 113 is provided. The shape of the slot 113 exactly corresponds to a detachable centrifuge insert which is used for accommodating the donation bag 3 and the product bags 5, 7 in respective chambers during the centrifugal process. During the centrifugal process, the cassette which is fixedly connected with the donation bag 3 serves as cover for the insert. Especially, the cassette covers the area accommodating the donation bag 3 of the insert. Thus, when the centrifugal process is finished, it is not necessary to detach the cassette from the insert, but the insert comprising the then filled product bags 5, 7 and the donation bag 3 with the buffy coat can be removed from the centrifuge and inserted into the slot 113.

After the insertion of the insert into the slot 113, a controller provided in the workstation automatically recognizes the insertion and causes the data detection process to be started by reading the data from the RFID tag. At the same time, a user deposites the plasma containing product bag 5 onto scales 107a and puts the tube 15 into a receiving section of the cutting/sealing device 105a. The erythrocyte containing product bag 7 is put onto scales 107b and its tube 17 is put into a receiving section of the cutting/sealing device 105b. Thereafter, the marking process as described above starts.

The cassette used in this embodiment, however, does not need to comprise the protrusions 104.

Figure 4:
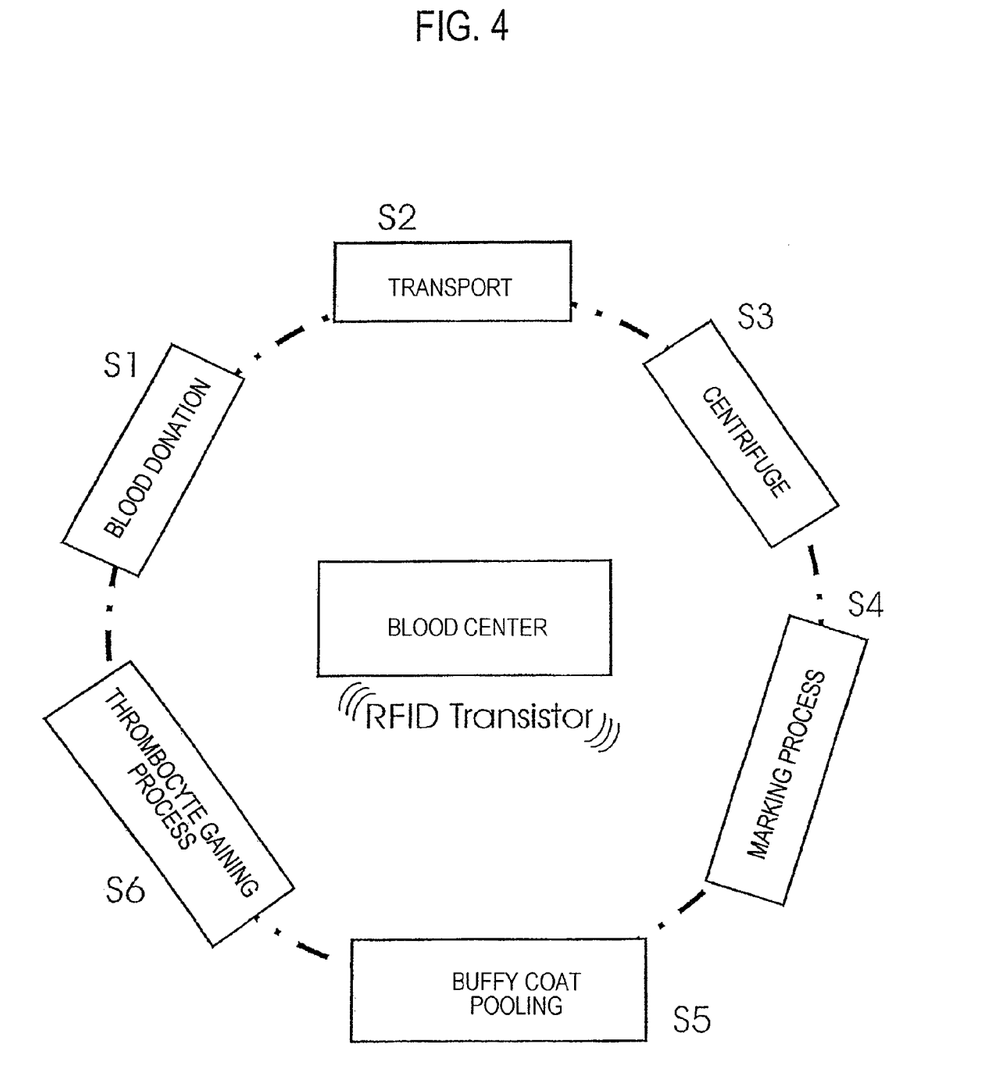
FIG. 4 shows a schematic diagram for understanding the advantages of the invention.

FIG. 4 shows a schematic diagram for understanding the advantages of the invention. That is, throughout the whole process the donated blood is accompanied by the cassette 1 having the RFID tag 19. That is, at the blood donation center, the donor's data are written onto the RFID tag 19. Then, the donor receives the cassette 1 having the donation bag 3 attached thereto. Via the tubes 15, 17, the product bags 5 and 7 are also in connection with the donation bag 3, however, the connection is interrupted by clamps (Step S1).

After the donation, information about the donation process can be stored on the RFID tag. The whole set is transported to a blood center for the further processing (step S2). There, the cassette 1 with the donation bag 3 and the product bags 5, 7 is put into an insert. Thereafter, a centrifugal process for separating the erythrocyte concentrate, the plasma and the buffy coat will take place (step S3).

After the centrifugal process, the insert together with the bags 3, 5, 7 is inserted into the slot 113 of the workstation for the marking process (step S4). Having separated and sealed the product bags 5, 7 at the workstation, the cassette 1, together with the donation bag 3 comprising the buffy coat, is brought to a buffy coat pooling process (step S5) in which buffy coats of different donors are put together for further processing. Due to the RFID tags 19 attached to the respective cassettes 1, in this process, it can be verified whether the plural buffy coats used in the process match each other. After the buffy coat pooling, the obtained buffy coat liquid is brought to a thrombocyte gaining process (step S6), where thrombocytes are extracted from the buffy coat liquid.

As alternatives of the embodiments described above, the following modifications are possible:

While the workstations in the above embodiments were described as more or less autonomous systems, it is possible to install a communication line with a central server, for instance a central server of a blood bank in a hospital. Thereby, an all time influence of the production process can be exerted, for instance it is possible to choose donation bags comprising blood of an urgently required blood group for an immediate processing.

Furthermore, a central control unit installed e.g. in the blood bank may control the separating and marking process via the workstation's controller.

Instead of at the cassette, the RFID tag can also be arranged at the donation bag. It only has to be ensured that the data from the reading device can be perfectly detected in the workstation.

Instead of printing paper tags which are stuck on the product bags by the user, the donor data and weight data can also be written in a memory of RFID tags and same can be attached to the product bags.

Alternatively, it is also possible to use product bags with integrated RFID tags whose memories are electronically written-in in the course of the marking operation. This is of advantage especially if the erythrocyte concentrate is filtered through the filter a second time and, then, gathered in the second product bag. In this case, after a repeated weighing of the second product bag, the then corrected weight can be written into the memory of the RFID tag. For this purpose, the RFID tag is ideally arranged at the second product bag.

Instead of starting the separating and weighing of the product bags only upon activation of the user, the correct positioning of the product bags and of the tubes can be automatically detected e.g. by sensors and the separating and weighing can be started automatically. A user can receive information if one of the bags is not yet optimally positioned.

The data cannot only be printed on the tags in the form of a bar code but can also be printed without a code so as to be readable by a person without technical aid or can be printed as a mixture of coded and uncoded data. Instead of printing the data onto tags they can also be printed directly onto the product bags by means of appropriate methods.

The tube leading from the donation bag to the product bag for the plasma can, in addition, lead through a filter serving as a leucocyte filter in order to filter white blood corpuscles out of the plasma. Also, the tube leading from the donation bag to the product bag for the erythrocyte concentrate may lead through a leucocyte filter in order to filter white blood corpuscles out of the erythrocyte concentrate.

While the embodiment has been described to the effect that, from the product bag for the erythrocyte concentrate, a tube leads from a filter to a second product bag, it is also possible to leave out the second product bag including the tube and filter. In such a case, the marking is effected directly on the product bag for the erythrocyte concentrate instead of on the second product bag.

While the invention is in particular suitable for marking containers containing blood products it is by no means restricted thereto but can be used for the production of containers containing liquids of any kind which are prepared in particular by a centrifuging process.

The scope of protection of the invention is defined exclusively by the attached claims.

The invention claimed is:

1. A workstation for marking containers (5, 7) containing a liquid, comprising:
    a connection surface (103) accommodating a replaceable cassette (1), the connection surface (103) including an RFID reading apparatus for detecting the data of the RFID tag integrated into the cassette (I),
    at least two trays (107*a*, 107*b*) for depositing respectively one outer container (5, 7) containing a liquid, wherein, to each tray, a second data detection device (107*a*, 107*b*) is assigned in order to detect data of the respectively outer container (5, 7) and
    a data processing device for processing the data detected by the RFID reading apparatus and the second data detection devices (107*a*, 107*b*), wherein,
    to each tray, a marking device (109*a*, 109*b*) for marking the respectively outer container (5, 7) is assigned, which is designed for marking a medium (111*a*, 111*b*) with data.

2. A workstation according to claim 1, wherein the respective second data detection device is designed as a pair of scales (107*a*, 107*b*) detecting a weight of the container (5, 7) deposited on the respective tray (107*a*, 107*b*).

3. A workstation according to claim 1 or 2, wherein, to each tray, a separation device (105*a*, 105*b*) is assigned for separating a connection means (15, 17) between the outer containers (5, 7) and a central container (3) arranged at the cassette (1), and the separation device (105*a*, 105*b*) is designed for sealing the interior of the respective container (5, 7) against the surrounding area in a fluid- or air-tight manner during separation.

4. A workstation according to claim 1, wherein the containers
    are designed as bags (3, 5, 7) or bottles and/or the connection means are designed as tubes (15, 17) and/or the separation device is designed as a hot-cutting and sealing device (105*a*, 105*b*) and/or the marking device is designed as a printing and/or labeling device (109*a*, 109*b*) or as an RFID writing device.

5. A workstation according to claim 1, wherein the marking device (109*a*, 109*b*} is designed for attaching the medium (111*a*, 111*b*} provided with the data to the container.

6. A workstation according to claim 1, wherein the connection surface (103} has guiding means (104, 113} enabling to insert the cassette (1) in a unique and predetermined manner, and preventing to insert the cassette (1) in another manner.

7. A method for marking containers filled with a liquid, comprising the following steps:
    a) insertion of a cassette provided with an RFID tag being integrated into the cassette (1) into a connection surface (103) of a workstation;
    b) detection of the data stored in the data storage device (19) by means of a data detection device;
    c) depositing at least two containers (5, 7, 9) connected, through a connection means (15, 17, 11), to a central container (3) provided at the cassette (1) and filled with a liquid on a respective tray (107*a*, 107*b*);
    d) detection of data of the container (5, 7, 9) by means of a second data detection device (107*a*, 107*b*) which is assigned to the respective tray (107*a*, 107*b*);
    e) processing the data detected by the data detection device and the second data detection devices (107*a*, 107*b*) by means of a data processing device;
    f) providing a medium (111*a*, 111*b*) with the processing data by means of a marking device assigned to the respective tray (107*a*, 107*b*};
    g) attaching the medium (111*a*, 111*b*} to a container (5, 7, 9) deposited on the tray (107*a*, 107*b*);
    h) separation of the connection means (15, 17) and fluid- and air tight sealing of the respective container (5, 7) against the surrounding area by means of a separation device (105*a*, 105*b*) assigned to each tray (107*a*, 107*b*).

8. A method for marking according to claim 7, wherein the data detection device is designed as an RFID reading apparatus and/or every second data detection device is designed as a pair of scales (107*a*, 107*b*) and/or the containers are designed as bags (3, 5, 7, 9) and/or the connection means are designed as tubes (15, 17, 11) and/or the separation device is designed as a hot-cutting and sealing device (105*a*, 105*b*) and/or the marking device is designed as a printing and/or labeling device (111*a*, 111*b*) or as an RFID writing device, and step g) is effected by manually or automatically attaching tags with processing data printed thereon or RFID tags with processing data written thereon to the respective container, the processing data including the data detected by the RFID reading apparatus and the weight detected by the respective pair of scales.

9. A method according to claim 8, wherein, on a tray (107*b*), a container (7) filled with a liquid and an empty container (9) connected with the latter are deposited, and the pair of scales (107*b*) detects the total weight of both containers (7, 9).

10. A method according to any of claims 7 to 9, wherein a communication line is established between the workstation and a central server.

* * * * *